United States Patent [19]

Ratcliff

[11] Patent Number: 4,575,804
[45] Date of Patent: Mar. 11, 1986

[54] DIET CALCULATOR

[76] Inventor: Lloyd P. Ratcliff, 306 Bayou Oaks Dr., Monroe, La. 71203

[21] Appl. No.: 518,947

[22] Filed: Aug. 1, 1983

[51] Int. Cl.[4] .............................................. G06F 15/42
[52] U.S. Cl. .................................... 364/715; 364/413; 364/567
[58] Field of Search .................. 364/715, 413, 567

[56] References Cited

U.S. PATENT DOCUMENTS

| 4,095,274 | 6/1978 | Gordon | 364/715 |
| 4,244,020 | 1/1981 | Ratcliff | 364/413 |
| 4,321,674 | 3/1982 | Krames | 364/413 |

OTHER PUBLICATIONS

Moran, "Electronic Diet Controller", *Computer Design*, Aug. 1977, pp. 116–118.

*Primary Examiner*—David H. Malzahn
*Attorney, Agent, or Firm*—Norvell E. Von Behren; Donna J. Thies

[57] ABSTRACT

A new and novel calculator for use by cooks, dieters and others is disclosed. The calculator may be made in a hand-held model and may be made in a scale version for use in the kitchen. The calculator permits instant access to counting of calories, carbohydrates and/or proteins and adding the amount of each item consumed. In the modified form of the invention a weighing mechanism is incorporated to accurately weigh each item to be consumed.

25 Claims, 10 Drawing Figures

| | | | |
|---|---|---|---|
| EGGS CHEESE & CEREAL<br>EGG<br>COTTAGE CHEESE 2½ OZ 30 | FRESH FRUITS<br>BERRIES ½ CUP<br>CANTALOPE ½ CUP<br>TANGERINE 46 | A. VEGETABLES<br>ASPARAGUS<br>CAULIFLOWER<br>CELERY<br>CUCUMBER<br>GREEN PEPPER<br>LETTUCE<br>MUSHROOMS<br>MUSTARD GREENS<br>RADISHES<br>SAUERKRAUT 60 | CANNED FRUIT<br>NO SUGAR ½ CUP<br>APRICOTS 72 |
| 1 OZ DRY CEREAL<br>1 OZ. COOKED 32 | APRICOTS<br>BANANA<br>CHERRIES 10<br>FIGS 2<br>GRAPEFRUIT ½<br>GRAPES 15<br>KIWI<br>KUMQUAT<br>MANDARIN<br>MANGO<br>NECTARINE<br>PEACH<br>PLUMS 2<br>STRAWBERRIES<br>UGLE<br>WATERMELON<br>1 CUP 48 | | APPLESAUCE<br>PEACHES 74 |
| BREAD<br>SLICE BREAD<br>ROLL 34 | | BROCCOLI<br>CABBAGE<br>KALE<br>SPINACH 62 | CHERRIES<br>PEARS<br>PINEAPPLE 76 |
| | | B. VEGETABLES<br>BEANS-WAX<br>BEETS<br>GREEN BEANS<br>SQUASH 64 | MEATS 3 OZ<br>BOLOGNA SLICE<br>SHELLFISH 78 |
| BUN 36 | | | |
| JUICES<br>MIXED VEG. 8 OZ. 38 | APPLE<br>ORANGE<br>PAPAYA ½<br>PINEAPPLE 50 | | HAM<br>LAMB<br>LIVER<br>FISH 4 OZ 80 |
| 40<br>GRAPEFRUIT 8 OZ<br>ORANGE 4 OZ<br>PRUNE 2½ OZ<br>TOMATO 8 OZ | PRUNES 52 | ARTICHOKES 66 | BEEF<br>FRANKFURTER<br>SAUSAGE<br>VEAL<br>CHICKEN<br>TURKEY 82 |
| | PEAR 54 | PEAS<br>PUMKIN 68 | |
| DAIRY<br>YOGURT<br>PLAIN 4 OZ. 42 | DRINKS<br>BOUILLON 56 | BRUSSELS SPROUT<br>CARROTS<br>EGGPLANT<br>OKRA<br>ONIONS<br>TOMATO<br>TURNIPS | |
| 44 BUTTERMILK 8 OZ<br>SKIM 8 OZ | COFFEE-BLACK<br>TEA-PLAIN<br>CARBONATED<br>NON CALORIE 58 | 70 | PORK 84 |

Fig.-3

DRINKS

| FOOD | CALORIES | CARBOHY. | PROTEIN |
|---|---|---|---|
| BEER | AC | ALJ | LC |
| CIDER | AJ | LEE | LC |
| COLA | AG | ELE | LC |
| FRUIT FLAVORED | AG | E | LC |
| FRUIT JUICES | AE | AG | LC |
| GINGER ALE | H | CLD | LC |
| LEMONADE | AB | ELJ | LC |
| ROOT BEER | AC | ALJ | LC |
| VEGETABLE JUICE | E | A | LC |
| WINE (DESSERT) | GK | G | LC |
| WINE (TABLE) | G | CLE | LC |
| WHISKEY (80 PRF.) | DB | K | LC |

BREADS

| FOOD | CALORIES | CARBOHY. | PROTEIN |
|---|---|---|---|
| BISCUIT | JC | H | CLD |
| BREAD | DK | AC | C |
| CEREAL (CORN) | AJ | CK | C |
| CRACKER | AEE | JA | K |
| CEREAL (BRAN) | FK | AF | C |
| CEREAL (WHEAT) | AKJ | AJ | E |
| GRITS | F | E | LC |
| PANCAKE | GK | LJE | A |
| PIZZA | FJ | F | G |
| PRETZEL | FK | LA | A |
| RICE | CE | G | A |
| SPAGH. & MTBALLS | CF | G | C |
| ROLL | B | CK | E |
| WAFFLE | DK | AK | G |

Fig.-5

DESSERTS

| FOOD | CALORIES | CARBOHY. | PROTEIN |
|---|---|---|---|
| CANDY (HARD) | AAK | A | LC |
| CANDY BAR | AGJ | AB | C |
| CAKE (ANGEL) | AEJ | CC | A |
| CAKE (FRUIT) | AAK | CC | A |
| CAKE (PLAIN W/ICING) | AAE | AB | A |
| COOKIE | AKK | EK | LC |
| CUSTARD | EK | E | A |
| FIG BAR | BJ | AJ | A |
| GINGER BREAD | AKK | AC | A |
| ICE CREAM | CF | G | A |
| JELLY | JD | AB | LC |
| PIE | JC | D | LC |
| PIE (PECAN) | BB | H | A |
| SHERBET | CC | J | LC |
| SIRUP | HK | AD | LC |

FATS

| FOOD | CALORIES | CARBOHY. | PROTEIN |
|---|---|---|---|
| BUTTER | AGK | K | LC |
| DRESSING (LOCAL) | EK | K | LC |
| DRESSING (HOME MADE) | AJK | K | LC |
| DRESSING (SALAD) | AEK | G | LC |
| GRAVY | CF | G | LC |
| MAYONNAISE | CKK | K | LC |
| PEANUT BUTTER | ACB | B | E |
| SALAD OIL | CGK | K | LC |

Fig.-6

MEATS

| FOOD | CALORIES | CARBOHY. | PROTEIN |
|---|---|---|---|
| BACON | JC | A | C |
| BEANS (DRIED) | EA | B | C |
| CHILI | EJ | E | E |
| CLAM | CC | BLA | E |
| CORN BEEF | JC | K | AK |
| CHICKEN (BROIL) | JK | A | B |
| EGG | JK | K | E |
| EGG OMLET | JJ | C | E |
| FISH (BROIL) | GJ | K | H |
| FISH (FRIED) | JK | C | G |
| FISH (CANNED) | JK | K | F |
| FOWL | BJ | K | B |
| LIVER | BJ | A | D |
| LUNCH MEAT | FJ | K | D |
| NUTS | CDK | C | C |
| OYSTERS | AJ | C | E |
| LOAF (MEAT) | BJ | A | G |
| MEAT WITH FAT | FJ | K | H |
| MEAT (LEAN) | DJ | K | H |
| POT PIE | JJ | J | C |
| SHRIMP | EE | A | J |
| SAUSAGE | BE | A | J |
| STEAK/CHOP | AAK | K | F |
| STEW (BEEF) | AG | E | C |
| TURKEY (BROIL) | JK | K | F |
| VEAL CUTLET | BC | K | F |

MILK PRODUCTS

| FOOD | CALORIES | CARBOHY. | PROTEIN |
|---|---|---|---|
| BUTTERMILK | AA | ALD | A |
| CHEESE | AAJ | LJ | B |
| CHOC. FLAVOR | CD | E | A |
| CHOC. SODA | CK | H | A |
| CHOC. SHAKE | GE | G | A |
| CHOCOLATE | AC | E | A |
| COCOA | EK | C | A |
| CONDENSED | ACJ | E | E |
| CUSTARD | JA | B | A |
| SOUR CREAM | JK | A | LC |
| EVAPORATED | JK | G | C |
| MALT | EA | E | A |
| SHERBET | CC | HLE | A |
| SKIM | AA | ALD | A |
| WHOLE | CK | ALJ | A |
| YOGHURT | AD | C | LJ |

Fig.-7

SNACKS

| FOOD | CALORIES | CARBOHY. | PROTEIN |
|---|---|---|---|
| CHIVES | A | A | LC |
| CORN CHIPS | FK | CK | C |
| DO-NUT | ACD | AC | C |
| FRENCH FRIES | FK | BLD | A |
| HAMBURGER | FJ | G | G |
| HOT DOG | AKK | G | G |
| OLIVES | EJ | C | LC |
| PICKELS | AK | A | LC |
| PIZZA | FJ | AG | G |
| POP CORN | AKF | EK | C |
| POTATO CHIPS | CEK | CK | A |

SOUPS

| FOOD | CALORIES | CARBOHY. | PROTEIN |
|---|---|---|---|
| ASPARAGUS | AG | A | A |
| BEAN W/PORK | CE | A | A |
| BEAN | AE | BLE | C |
| BEEF NOODLE | H | C | A |
| BOUILLION | AK | K | A |
| BROTH | AK | LD | A |
| CHICKEN W/RICE | D | CLE | A |
| CHICKEN NOODLE | D | CLE | A |
| CLAM CHOWDER | AA | ELE | C |
| MINESTRONE | AG | A | A |
| MUSHROOM | AF | E | LC |
| OYSTER STEW | AB | E | A |
| SPLIT PEA | AF | F | A |
| TOMATO | AC | B | LC |
| VEGETABLE | AA | GLE | A |
| VEGETABLE BEEF | AJ | A | C |

Fig.-8

| VEGETABLES & FRUIT | | | |
|---|---|---|---|
| FOOD | CALORIES | CARBOHY. | PROTEIN |
| BEANS (DRIED) | AE | D | C |
| BEANS (GREEN) | E | A | ALJ |
| CORN ON COB | AE | G | LJ |
| DATE | GJ | E | A |
| FRUIT (RAW) | AD | G | LC |
| FRUIT (COOKED) | AD | B | LC |
| FRUIT (PRE-SWEET COOKED) | CC | H | LC |
| FRENCH FRIES | FK | F | A |
| GREENS | B | LF | LJ |
| SWEET POTATO | CD | B | A |
| RAISN | AKD | H | A |
| VEGETABLES (RAW) | E | C | A |
| VEGETABLES (COOKED) | AK | C | A |

Fig-9

DIET CALCULATOR

BACKGROUND OF THE INVENTION

This invention relates generally to calculators and more particularly to a new and novel calculator improvement whereby a person is able to quickly determine the caloric, carbohydrate and/or protein value of a given portion of food or drink without resorting to endless tables contained in booklets or various charts as is the usual practice.

It is a recognized fact that many overweight people in the world are constantly trying to lose weight by various methods such as diets, by restricting their caloric, carbohydrate and/or protein intake and many other systems.

One of the most popular ways of restricting one's diet is to purchase a lengthy book which will list every known portion and type of food along with the caloric, carbohydrate and/or protein value of the food item. Thereafter the dieter resorts to looking up the appropriate food or drink in the charts contained therein and generally either tries to remember the value or mentally adds it to other values of consumable items or else writes down the value on a separate piece of paper as the items are consumed. It can be seen that this method, while being accurate, can be very burdensome to many people, especially businessmen and women who travel extensively and must eat out in restaurants during their trips. It is also very burdensome to the average housewife who is attempting to prepare a proper meal for her family since it slows her down drastically by requiring her to constantly go into the book to find the appropriate food value.

It has been estimated that there are approximately one-hundred million overweight Americans and at least another seventy million watching their weight with a daily goal of staying trim and healthy. At least seventy million Americans are estimated to start on some type of a diet each year, many of which end in total failure.

CROSS-REFERENCES TO RELATED APPLICATIONS

U.S. Pat. No. 4,244,020, issued Jan. 6, 1981, to Lloyd P. Ratcliff and entitled, "Caloric and/or Carbohydrate Calculator."

SUMMARY OF THE INVENTION

In order to overcome problems inherent in the before-mentioned methods for accomplishing the objective of losing weight, there has been provided by the applicant's invention a new and improved calculator which allows the user to have access to counting calories, carbohydrates and/or proteins instantly to thereby permit him to instantly tabulate or count the amount of calories, carbohydrates and/or proteins in a given portion of food or drink.

The calculator comprises a numerical calculator electrical operation circuit contained within a case with the circuit containing at least a memory add circuit as well as other circuits and contacts. The calculator keyboard has been modified to provide a plurality of first buttons which have indicia formed thereon designating groups of ingestible items such as food or drink. The items formed on each button are grouped together by caloric, carbohydrate and/or protein value and have a substantially similar value as grouped so that when a particular first button is pushed on the calculator, a given caloric, carbohydrate and/or protein value will be recorded in the circuit. A second button, positioned on the keyboard and electrically connected to the calculator circuit, functions as an add button to add the given caloric, carbohydrate and/or protein values recorded in the circuit whenever the first buttons are pushed. A standard numerical display readout is positioned in the calculator case and is electrically connected to the circuit to display the total caloric, carbohydrate and/or protein value of the items pushed on the first plurality of buttons.

In a modification of the invention, there is provided a calculator in combination with a weighing mechanism which is contained within the calculator case. The weighing mechanism has a weighing platform positioned on the exterior of the case to receive ingestible food items which are positioned on top of the platform. The case has viewing means for viewing various ingestible items on a viewing screen with the items as viewed containing a food code positioned in proximity to the item as listed. Means are contained on the case for entering into the calculator the food code viewed on the viewing means and also for obtaining the caloric carbohydrate and/or protein value of the ingestible item positioned on top of the platform. The viewing means contains means for reading the caloric carbohydrate and/or protein value of the ingestible item positioned on top of the platform and the calculator contains a numerical calculator electrical operation circuit contained within the case and electrically connected to the viewing mechanism, the viewing means and the other parts of the invention.

By using the modification to be described more fully hereinafter, the user of the device can simply weight a given portion of food and/or drink and then accurately and quickly calculate the caloric, carbohydrate and/or protein value of the item.

Accordingly it is an object and advantage of the invention to provide an improved calculator having a modified keyboard which allows the user of the device to quickly calculate the caloric, carbohydrate and/or protein value of the food consumed without resorting to lengthy tables as is the past practice.

Another object and advantage of the invention is to provide a new and novel calculator modification which combines a basic four-function calculator having addition, subtraction, multiplication and division circuitry with a book or table having numerical values representing caloric, carbohydrate and/or protein values of various food and drink items.

Still yet another object and advantage of the invention is to provide a new and novel calculator which may b used by businessmen and businesswomen while traveling and eating out in restaurants without having to resort to lengthy charts or bulky books in order to find the appropriate caloric, carbohydrate and/or protein value of the item to be consumed.

Another object and advantage of the invention is to provide a new and novel calculator which may be used with a modified weighing scale by a housewife or cook to quickly and accurately calculate the caloric, carbohydrate and/or protein value of a food and/or drink item.

These and other objects and advantages of the invention will become apparent from a review of the drawings of the invention and from a reading of the description of the preferred embodiment.

BRIEF DESCRIPTION OF THE DRAWINGS

FIG. 3 is an enlarged view of a portion of the modified calculator keyboard showing the plurality of contacts and indicia hereinbefore described used with the calculator keyboard;

FIGS. 5-9 show projections on the viewing screen of the FIG. 4 versions; and

DESCRIPTION OF THE PREFERRED EMBODIMENT

Figure 1:
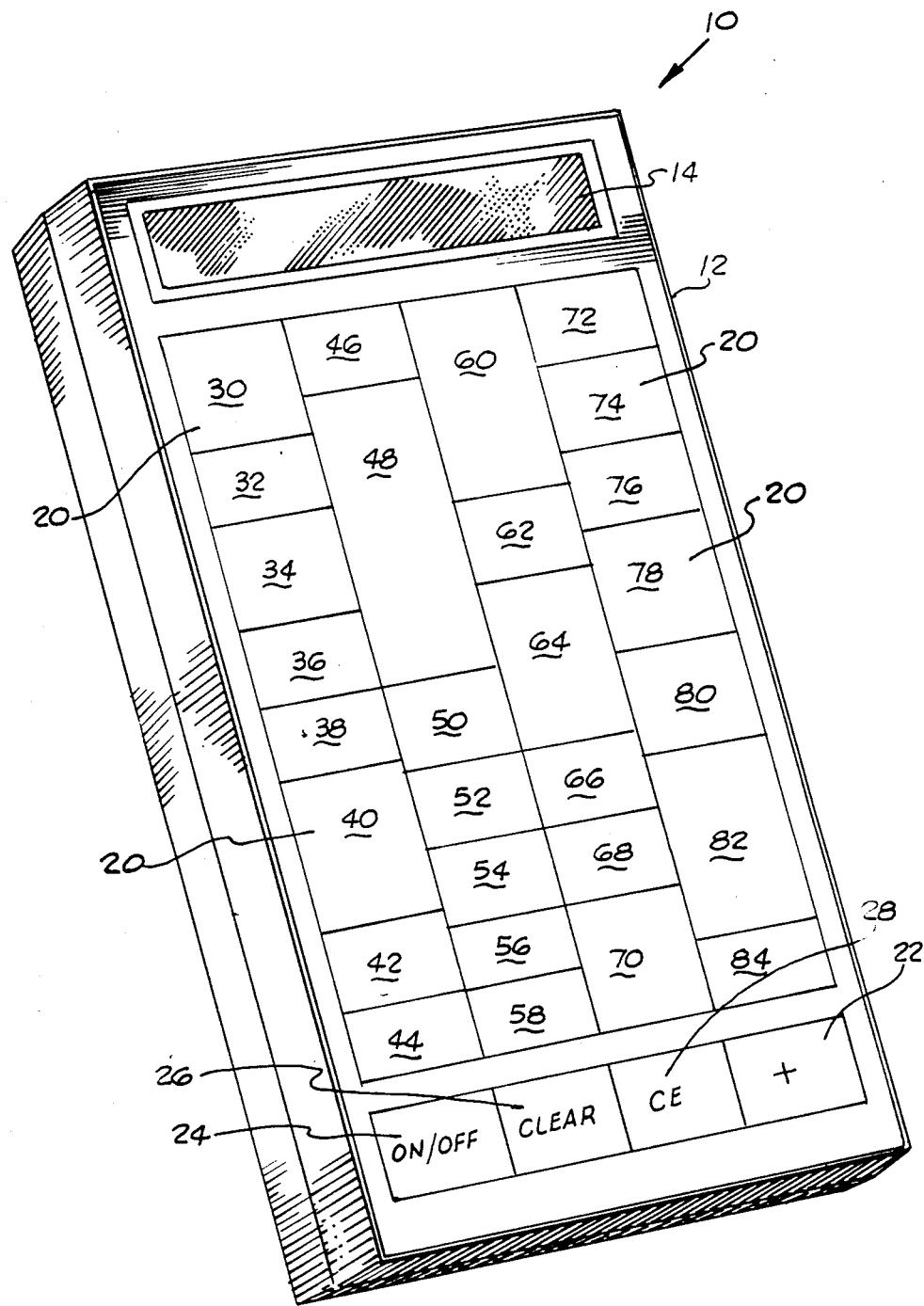
FIG. 1 is a perspective view of the applicant's new and improved caloric, carbohydrate and/or protein calculator showing the modified calculator keyboard having the plurality of contacts and indicia hereinbefore described.
Figure 2:
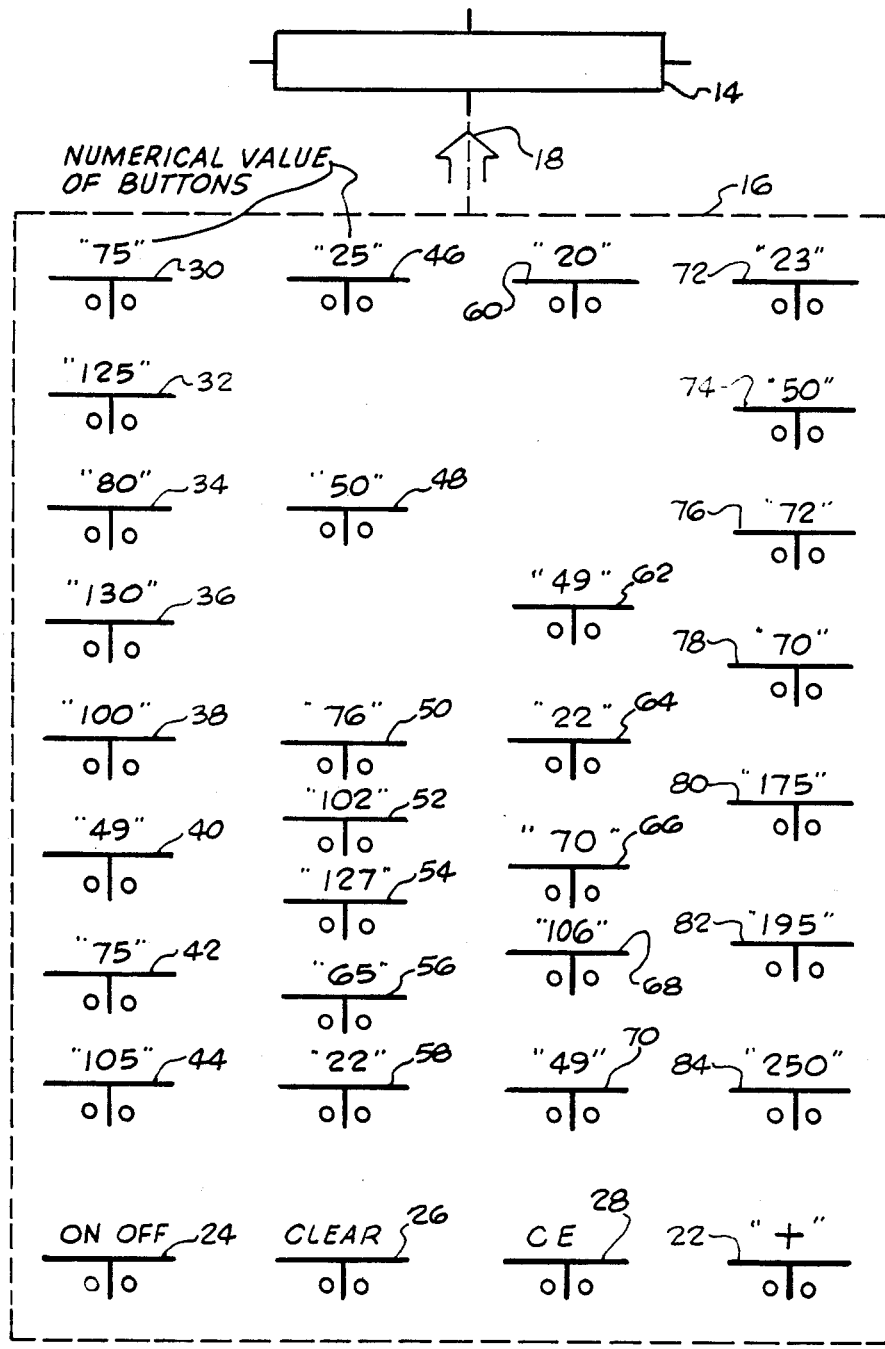
FIG. 2 is a schematic view of the electrical circuitry modifications necessary to modify the standard numerical calculator electrical operation circuit so that the modified calculator keyboard shown in FIG. 1 may be utilized.

Referring now to the drawings in general and in particular to FIGS. 1, 2 and 3 of the drawings there is shown the applicant's hand-held diet calculator generally by the numeral 10 which comprises a calculator case 12 containing a numerical calculator electrical operation circuit of the type formerly used in hand-held calculators. The electrical operation circuit contains at least a memory add circuit as well as other circuits and contacts.

A standard numerical display readout 14 is positioned in the calculator case and is electrically connected to the electrical circuit to display the total numerical value of the items pushed on the diet calculator buttons. For purposes of clarity, in FIG. 2 the electrical operation circuit is shown within the dashed line 16 and the connection to the readout would be numeral 18 as shown. The modifications in the applicant's hand-held calculator relate to changes in the normal buttons and number value of the buttons appearing on a standard calculator so that the modified calculator may be used specifically for dieters.

It can be seen in FIG. 1 how the applicant's calculator has modified a standard calculator keyboard by having a plurality of first buttons 20 of different sizes and shapes, the purpose of which will be explained more fully hereinafter.

At least a second button 22 is positioned on the applicant's modified board and is electrically connected to the operational circuit with the second button functioning as an add button to add a given numerical value recorded in the circuit whenever the first plurality of buttons are pushed. The calculator may also contain other buttons within the spirit and scope of the invention such as an "on/off" button 24 functioning to turn the calculator on and off. In addition a "clear" button 26 may be utilized to clear the entire calculator of the input previously put into the calculator. In a like manner, a "CE" button 28 may be utilized to clear a particular individual error in a manner similar to a standard calculator.

Referring now to FIGS. 1 and 2 of the drawing there will be seen how the standard numerical calculator electrical operation circuit may be modified along with the modification of the buttons on the face of the calculator in order to achieve the applicant's novel purpose with his diet calculator. As has been before mentioned a plurality of first buttons 20 are positioned on the keyboard. In the applicant's preferred embodiment, his keyboard is formed of four rows of vertical buttons 20. The first or left-most row of buttons 20 are designated in FIG. 1 with the numerals 30, 32, 34, 36, 38, 40, 42 and 44. The second vertical row of buttons are numbered 46, 48, 50, 52, 54, 56 and 58.

In the third row vertical buttons, the first buttons are numbered 60, 62, 64, 66, 68 and 70 while the fourth row of first buttons are numbered 72, 74, 76, 78, 80, 82 and 84. It can be seen by referring to FIG. 2 how each button is connected to the electrical circuit and represents a specific numerical value which is pushed into the calculator circuit when the particular button is pushed. For example when the button 30 is pushed the numerical value 75 is inserted into the calculator circuit. In a like manner when the button 32 is pushed the numerical value 125 is inserted into the circuit. A pushing of button 34 will insert 80 into the electrical circuit while a pushing of button 36 will insert 130 into the electrical circuit. It can be seen then in FIG. 2 how the numbers positioned over the switches represent the numerical value of the insertion into the calculator circuit for each particular button.

By referring to FIG. 3 of the drawing there is shown an enlarged view of a portion of the modified calculator keyboard showing the plurality of buttons or contacts and the indicia which is printed on the buttons and is used by the person owning the calculator. Each first button 20 which has been specifically numbered from the numeral 30 to the numeral 84 contains groupings of ingestible food and drink items which have been grouped by a numerical value and placed on the appropriate button. The numerical value may be by groupings of calories, carbohydrates, proteins or some other particular grouping. For example in the embodiment shown in FIG. 2 the particular numerical values for each key would be by grouping of caloric values. If the applicant's diet calculator were made to be used by a dieter who preferred to watch carbohydrates, then the particular numerical value for each key would obviously change to be a different number. In a like manner the numerical value for proteins would be different and the particular groupings of items may also be different depending upon whether the items were carbohydrates, proteins, calories or what other items were to be grouped.

In grouping of the particular items, it has been found, for example, that eggs, cheese and ceral which are grouped and printed on button 30 would all be approximately 75 calories. That is to say, one egg or two-and-a-half ounces of cottage cheese would each be 75 calories. In a similar manner the grouping for juices on button 40 would all be 49 calories with an eight ounce grapefruit, a four ounce orange, a two-and-a-half ounce prune and an eight ounce tomato all being approximately the calorie values. It can be seen then that the user of the diet device, should it be constructed for calories as is shown in FIGS. 1, 2 and 3, would simply carry the diet calculator with him and upon eating a meal would punch the appropriate first button for each item that he ate. He would then punch the second button 22 which is a plus button and continue punching the first button 20 using the calculator to add the individual items consumed. As each first button 20 is pushed followed by a second button 22 adding the total, the dieter is then able to see a running total of the items consumed. After the last first button 20 has been pushed then the dieter would again push a plus button 22 in order to get the final total of his meal. Thereafter he could simply write this total down for the meal and add up the next meal separately as he consumed it.

From the foregoing it can be seen that the applicant's calculator may be used in the preferred embodiment as a calorie calculator and may also be used as a carbohydrate calculator and a protein calculator as well as in other diet groupings as preferred by the user. The modifications in the calculator keyboard and circuitry would be made accordingly within the spirit and scope of the invention. The caloric, carbohydrate and protein numerical value of the buttons are given in the claims.

It has been found from experimentation that the grouping of items shown in FIG. 3 of the drawing and the paritcular quantities listed on the first buttons 20 numbered from 30 to 84, are the usual size of food and drink encountered by most people. This grouping then allows the calculator to be used by the dieter when he is away from home in a restaurant since the calculator contains normal quantities often served in most restaurants. If the user desired a special diet prescribed by a physician, then an individual calculator could be configured using the items required by the physician.

By grouping the numerical values of calories, carbohydrates or proteins as shown in FIG. 2 of the drawing and positioning a special first button 20 above each button having the appropriate food or drink item printed thereon, the user of the device is able to eliminate a complicated book listing the values of all of the foods. Since the applicant's calculator as modified has combined the features of a book with the features of a calculator, then it provides a much more useful tool for the dieter encouraging him to complete his task.

Referring now to FIGS. 4–10 there is shown the modifications in the applicant's diet calculator wherein the calculator is made as a freestanding unit shown generally by the numeral 86. The unit comprises a case 88 having a viewing screen 90 positioned within the case. A platform weighing scale mechanism is positioned partially on the exterior of the case and contains a platform 92 for receiving quantities of ingestible items placed on the platform. The platform 92 is carried by a vertical beam 94 which is carried by the internally positioned weighing mechanism used with the applicant's invention.

The case 88 contains a plurality of first buttons 96 positioned in two rows on the face of the case. The first buttons have positioned thereon indicia designating various ingestible items. In the embodiment shown in FIG. 4, the first row of first buttons would contain the indicia "drinks", "breads", "desserts", "fats", and "meats". The second row of first buttons would contain indicia designating the items "milk products", "snacks", "soups" and "vegetable fruits".

A plurality of second buttons 98 would also be positioned on the case and would have positioned thereon indicia designating food code values. In the embodiment shown in FIG. 4, the second buttons 98 would comprise the twelve buttons shown in three rows on the face of the case 88 and would have the letters A-H applied on the first row of buttons and the letters J-L on the second row of buttons with the last row containing a button with the letter M designated on the button. The purpose of the second buttons 98 will be described more fully hereinafter when describing the function of the viewing screen in the overall diet calculator.

Figure 4:
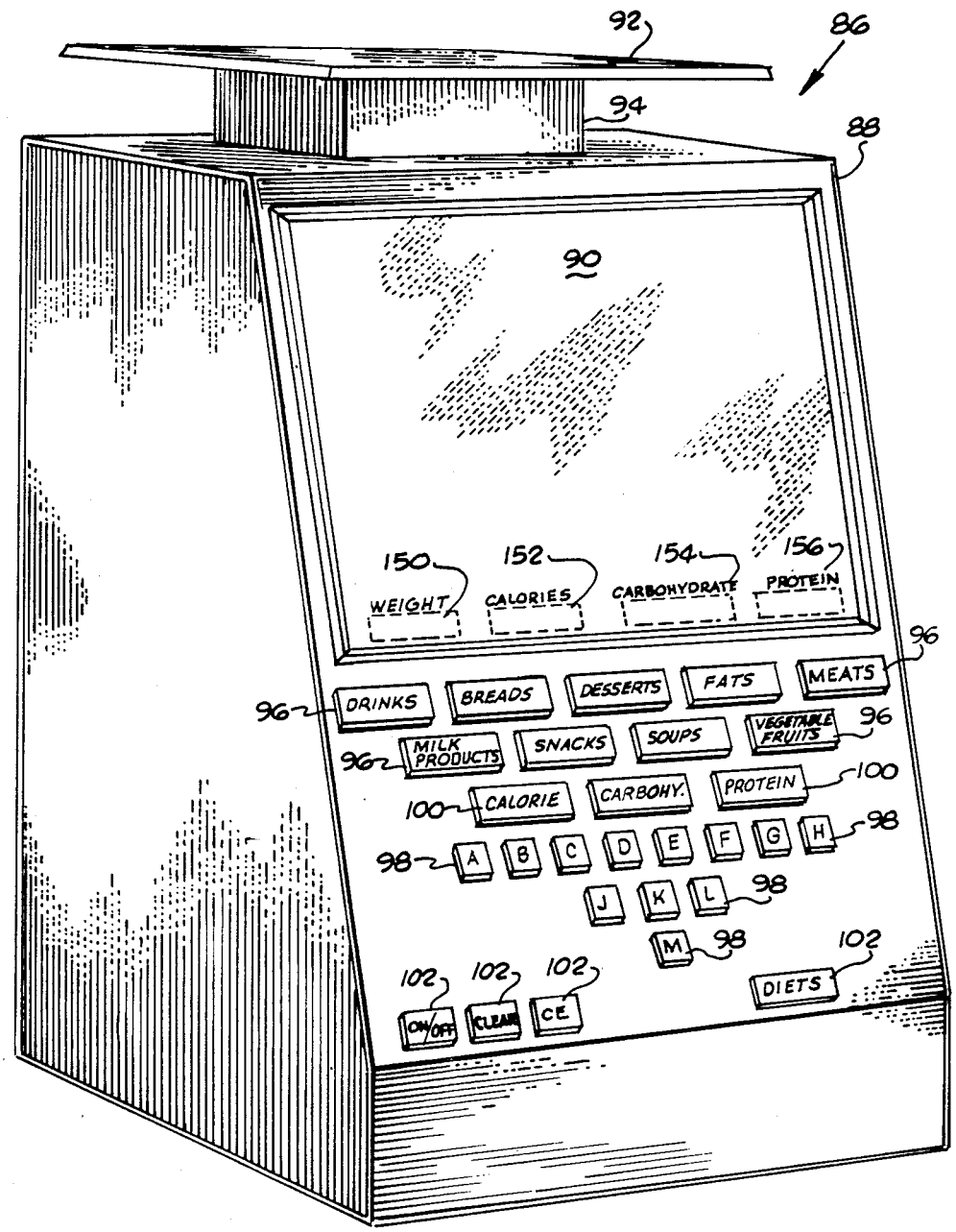
FIG. 4 is a perspective view of the applicant's modified calculator using a combined calculator/computer in combination with a weighing scale for use by a cook or housewife.

A plurality of third buttons 100 would be positioned on the case 88 and in the embodiment shown in FIG. 4 would comprise a single row of three buttons having the indicia positioned thereon designating at least one item from a group of items comprising "calories", "carbohydrates" and/or "proteins". The purpose of the third buttons 100 will also be detailed more fully hereinafter when referring to the viewing screen's function in the applicant's overall device.

A plurality of fourth buttons 102 are positioned on the case 88 and have positioned thereon indicia designating miscellaneous calculator functions as shown in FIG. 4 of the drawings. In the embodiment shown the fourth buttons would comprise the bottom row of buttons in FIG. 4 having the designation "on/off", "clear", "CE" and "diets". Other arrangements of the various first, second, third and fourth buttons on the calculator are within the spirit and scope of the invention and the arrangement of the viewing screen 90 in relation to the buttons and the scale platform 92 is also within the spirit and scope of the invention.

Referring now to FIGS. 5–9 of the drawing there are shown representations of the viewing screen 90 and what would be projected on the viewing screen at the appropriate time when the applicant's device was used. In FIG. 5 there are shown two projections of the viewing screen 90 with one projection shown at 104 which would be the viewing screen as it appeared whenever a predetermined quantity of drink items was positioned on the viewing screen. In a similar manner the viewing screen could have a predetermined quantity of breads positioned on the screen as shown at 106 as the user of the device desired.

When the ingestible items are positioned on the viewing screen as will be discussed more fully hereinafter, they will be grouped in a plurality of columns with the first column 108 having listed thereunder the various food and drink items such as beer, cider, cola, etc. In the second column 110 would be listed the calories while a third column 112 would list carbohydrates and a fourth claim 114 would list proteins for the various drink items. Under each of the columns 110, 112 and 114 would be listed the various food codes 116 which be in the form of a single or multiple grouping of letters such as beer calories "AC", beer carbohydrates "ALJ" and beer proteins "LC". The food code letters 116 correspond with the letters positioned on the second buttons 98 and there use will be described more fully hereinafter.

When changing the viewing screen 90 from drinks 118 to breads 120, the user of the device would then be able to view a different grouping of food items which is the display shown in the screen projection 106 of FIG. 5. In a similar manner the calories 110, carbohydrates 112 and proteins 114 would also be displayed with columns containing the various food code letters 116.

In a similar manner when the user of the device desires to view dessert items 122 he would change the viewing screen projection to that shown in 124 and would view the food items 108 under desserts such as candy, cake, cookies, etc. and would also be able to view the calories 110, carbohydrates 112 and proteins 114 with their appropriate food code letter or letters 116 positioned in vertical columns below. By switching the screen 124 to view fats 126, the diet calculator user would then view the viewing screen 128 as shown in FIG. 6 of the drawing and would be able to view the various fat items such as butter, dressing, gravy, etc. with its appropriate listing of calories 110, carbohydrates 112 and proteins 114 and their appropriate food codes 116 positioned in vertical columns.

FIG. 7 shows a representation of two of the viewing screen projections with the viewing screen 130 showing a plurality of meat items 132 while the viewing screen 136 shows a plurality of milk products 134. When viewing the meat items 132 on the viewing screen 130 the user would then be able to view a plurality of food items 108 such as bacon, beans, chili, etc. and also the calories 110, carbohydrates 112 and proteins 114 positioned in vertical columns having the appropriate food code letter 116 positioned underneath the columns. Milk products 134 would be viewed on the viewing screen 136 by pressing the appropriate button as will be described hereinafter to view the plurality of food items 108 such as buttermilk, cheese, chocolate flavor, etc. with their appropriate calories 110, carbohydrates 112 and proteins 114 and their associated food code letters 116.

FIG. 8 shows a representation of the viewing screen showing a plurality of snack items 138 being projected on the screen 140 with the appropriate food items 108 being chives, corn chips, donuts, etc. with their appropriate calories 110, carbohydrates 112 and proteins 114 having the food code letters 116 positioned there below. By switching the view on the viewing screen from 140 to that shown at 144, the dieter would then be able to view a plurality of soups 142 having the food items 108 listed such as asparagus, bean with pork, bean, beef noodle, etc. having the appropriate calories 110, carbohydrates 112 and proteins 114 listed on the screen along with the appropriate food code letters 116.

FIG. 9 shows a viewing screen grouping 148 having a plurality of vegetables and fruits 146 which could be viewed on the viewing screen with the applicant viewing the food items 108 such as beans (dried) "beans" (green), corn on the cob, etc. having the appropriate calories 110, carbohydrates 112 and proteins 114 along with their appropriate food code letters 116 positioned in vertical column on the viewing screen.

The various viewing screen representations 104, 106, 124, 128, 130, 136, 140, 144 and 148 may be supplemented by other viewing screen projections in the applicant's device as may be desired and the food items 108 shown under the various categories such as drinks 118, breads 120, desserts 122, fats 126, meats 132, milk products 134, snacks 138, soups 142 and vegetables and fruit 146 may be expanded as desired by the manufacturer of the device in order to provide much expanded listings of food items on the viewing screen 90. It is within the spirit and scope of the invention that the applicant's device may be constructed with at least one of the groupings of items listd such as calories 110, carbohydrates 112 or proteins 114 and may also be constructed with two or three of these items. In other words, should a less expensive version of the applicant's device be used then the viewing screen 90 may be used to view only calories 110 instead of the three combinations of calories 110, carbohydrates 112 and proteins 114 shown in the embodiment of FIG. 4.

As an alternate in the projection of the food items 108 on the viewing screen 90 with the food code value being positioned before the food item 108 and by the manipulation of the buttons of the calculator, all three items of calories 110, carbohydrates 112, and proteins 114 could be programmed to register at once on the viewing screen.

Referring back to FIG. 4 of the drawing the applicant's device is designed to utilize the viewing screen 90 also to be able to view the weight 150 of the food item positioned on the platform 92. The weight in ounces would register on the viewing screen 90 at the position shown at 150. The applicant's device would also be programmed so that the calories 152, the carbohydrates 154 and the proteins 156 would be registered on the viewing screen 90 at the appropriate place shown in FIG. 4 of the drawing. When constructed thusly it can be seen that the user of the device has a totally complete, self-contained unit which allows a food item to be placed on the platform 92 and by the appropriate manipulation of buttons to determine the calories, carbohydrates and/or proteins of the item put on the scale, by weight.

In the preferred embodiment of this modification of the applicant's basic diet calculator, the viewing screen 90 is designed to be a cathode ray tube (CRT) and is capable of showing the various items hereinbefore described when referring to FIGS. 5-9. It is within the spirit and scope of the invention that the viewing screen 90 could also be a mechanical device which could be turned by hand to view the various items and the remaining portion of the calculator could be a modified calculator of the type designed to function as will be described hereinafter.

Figure 10:
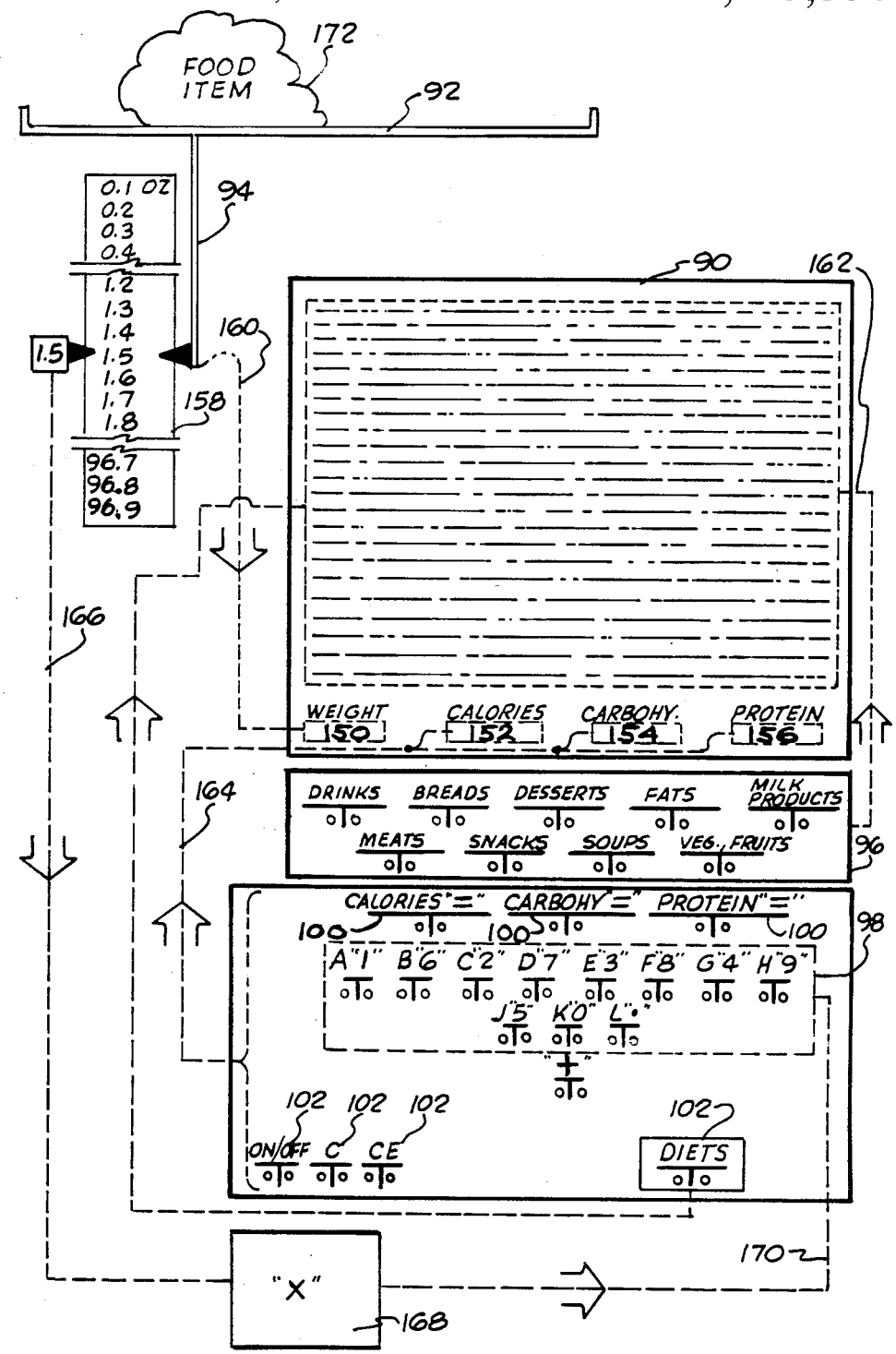
FIG. 10 is a schematic view of the electrical circuitry modifications of the calculator/computer circuitry used in the FIG. 4 version of the applicant's invention.

Referring now to FIG. 10 of the drawing there is shown a schematic of the internal items of the applicant's unit 86 which comprises the before-mentioned viewing screen 90 and calculator means positioned within the case for electrically connecting the viewing screen 90, the scale mechanism 92 and 94 and the plurality of first buttons 96, second buttons 98, third buttons 100 and fourth buttons 102 together as a functioning calculator.

When constructed as a cathode ray tube (CRT) viewing screen 90 in combination with the calculator/computer circuit shown in FIG. 10, then the applicant's device becomes a combination computer/calculator which has been programmed and electrically connected to project on the viewing screen 90 on command the various food items shown in FIGS. 5-9 of the drawings.

The weighing device of the applicant's invention comprises the before-mentioned weighing platform 92 attached to the weighing beam 94 and having the appropriate weighing mechanism 158 positioned within the case 88. The weighing mechanism would be designed to register the appropriate weight in one-tenths of an ounce on the viewing screen 90 at the position shown by the numeral 150 by means of the electrical connections 160.

As has been before mentioned, the plurality of first buttons 96 are positioned on the case and are electrically connected at 162 to the computer/calculator circuit to signal the computer to project a given group of ingestible items on the viewing screen.

The plurality of second buttons 98 positioned on the case are electrically connected to the computer/calculator circuit at 164 to send the appropriate signal to the viewing screen to indicate the appropriate calories 152, carbohydrates 154 and/or proteins 165 on the viewing screen 90. The plurality of second buttons 98 are also electrically connected at 166 to the weighing mechanism 158 and to a multiplier 168 connected to the buttons 98 through the electrical connection 170 to properly record the weight of the food item in the calculator circuit. For example as an ingestible food item 172 is positioned on the platform 92, the weighing mechanism 158 will sense the weight such as 1.5 ounces as shown in FIG. 10 of the drawing. The weighing mechanism 158 will then send a signal through electrical connection 166 to the automatic multiplier 168 to tell the computer circuit to multiply the figure 1.5 times the number pushed by the second plurality of buttons 98. As the user of the device views the appropriate food item on the viewing screen 90 he would then read the appropriate food code 116 for that item and would push the appropriate button or buttons 98. This would then multiply the numbers pushed on the buttons to get the proper value of calories, carbohydrates and/or proteins.

The second plurality of buttons 98 have been electrically connected to the computer circuit to register the following numerical values:

| Button Number | Numerical Value |
| --- | --- |
| A | 1 |
| B | 6 |
| C | 2 |
| D | 7 |
| E | 3 |
| F | 8 |
| G | 4 |
| H | 9 |
| J | 5 |
| K | 0 |
| L | "." |
| M | "+" |

The applicant has determined the appropriate calories, carbohydrates and/or proteins for each of the ingestible items shown on the viewing screen 90. By assigning a letter code to the calories, carbohydrates and/or proteins as shown in FIGS. 5-9 using the numerical value above listed for the second plurality of buttons 98, then the user of the device can simply punch letter combinations shown as indicia formed on the button face 98 as shown in FIG. 4 of the drawing. This simplifies the use of the calculator for the average housewife and elderly person who may be intimidated using a calculator and punching numbered buttons. In addition by the use of the weighing mechanism 158 with its attached weighing platform 192, the weight of the food item 172 is automatically figured for the housewife using the device so that the applicant's new and novel invention is much simplified providing an attractive selling feature for a kitchen user. The use of the automatic multiplier 168 in the computer circuit to multiply the weight of the food item 172 also greatly simplifies the use of the device.

Since the weight of the food item 172 is displayed on the viewing screen 90 and also the calories, carbohydrates and/or proteins may be obtained for viewing on the screen at 152, 154 and/or 156, the housewife is then able to change the portion of the food item 172 should the amount be too great by simply removing a portion of the item reading again the new weight and calories, carbohydrates and/or proteins.

To display the various ingestible items shown in FIGS. 5-9 of the drawing, the user of the device will first push the "on/off" button 102 and then will push the "diets" button 102 positioned at the right corner of the case 88. This will then project on the viewing screen 90 the ingestible item desired. To select various ingestible items which are chosen from the first buttons 96, the housewife would then punch one of the plurality of first buttons 96 to view that ingestible item. For example if she were preparing a portion of hamburger, she would push the first button 96 having the indicia printed on the button "meats". At that time the viewing screen 90 would project in the manner shown in FIG. 7 the various kinds of meats 132 shown on the viewing projection 130. The housewife would then simply run her finger down to the appropriate meat item and would read the appropriate calorie food code letter. For example if the item were liver she would read the food code BJ and would then punch the second plurality of buttons "B" and "J" which would then automatically give her the total of calories projected at 152 on the viewing screen 90. If the housewife wanted to know the carbohydrate value of the liver item 172 that she had placed on the scale then she would punch the letter code A in the second plurality of buttons 98 and would then total the item by punching the third plurality of buttons 100 having the indicia "carbohydrates" printed on the button. Since all three of the third plurality of buttons 100 function as equal buttons in the calculator circuit, then their purpose is to find the total sum of the calories, carbohydrates and/or proteins for the particular food item 172.

From the foregoing it can be seen that the applicant's new and novel device allows the housewife to compute very precisely the exact weight, calories, carbohydrates and/or protein value of a given quantity of food positioned on the weighting platform 92. This is able to be done by the use of simply pushing a plurality of few buttons having indicia formed on the buttons making the job easier and less intimidating for the average housewife.

It is within the spirit and scope of the invention that other diet items of ingestible products may be programmed within the calculator when used with that version and the applicant is not to be limited to the exact diet items shown in FIGS. 5-9 of the drawings. In addition other variations may be incorporated into the applicant's invention within its spirit and scope such as a rearrangement of the various first, second, third and fourth buttons and also the values of the various food code items. Other changes may be made within the spirit and scope of the invention such as a rearrangement of the placement of the weighing platform 92 in relation to the viewing screen 90 and the placement of the various buttons on the case 88. Other features may also be incorporated into the invention to further make the invention less intimidating to the average user and yet still provide the accuracy needed in order to control one's diet.

There has been shown by the applicant's invention as shown in FIGS. 1-3 using the hand-held calculator version and by the modification shown in FIGS. 4-10 using the combination calculator/computer version how a complete use of both versions may be advantageously used by the dieter. For example by the purchase of a hand-held version shown in FIGS. 1-3 the dieter is able to roughly calculate items which he would purchase at a restaurant or take to work in a brown bag. His wife could purchase and use the scale version shown in FIGS. 4-10 in preparing the home meals such as supper for the entire family. With the applicant's invention in its preferred form and modification it can be seen that the spirit and scope of the invention and its objects and advantages have been achieved to allow the user of the device to have access to counting calories, carbohydrates and/or proteins instantly to thereby permit an instant tabulation or count of the calories, carbohydrates and/or proteins in a given portion of food or drink. The use of the applicant's device in its preferred embodiment form and modified form also allows the applicant to disregard the many calorie books having lengthy and time-consuming listings of various food items for diet purposes.

Having described my invention, I claim:

1. A diet calculator, comprising:
   (a) a calculator case;
   (b) a standard numerical calculator electrical operation circuit contained within the case, the circuit containing at least a memory add circuit as well as other circuits and contacts;
   (c) a modified calculator keyboard positioned on the calculator case;
   (d) a plurality of first buttons positioned on the keyboard and having formed thereon indicia designating groups of ingestible items, the plurality of first buttons being electrically connected to the standard numerical calculator electrical operation circuit so that each button when pushed represents a number in the standard numerical calculator electrical operation circuit, the items formed on each button being grouped together by a numerical value and having a substantially similar numeric value as grouped so that when a particular first button is pushed on the calculator, a given numerical value will be recorded in the standard numerical calculator electrical operation circuit;
   (e) a second button, positioned on the keyboard and electrically connected to the standard numerical calculator electrical operation circuit, the second button functioning as an add button to add the given numerical values recorded in the standard numerical calculator electrical operation circuit whenever the first buttons are pushed; and
   (f) a standard numerical calculator display readout positioned in the calculator case and electrically connected to the standard numerical calculator electrical operation circuit to display a total numerical value of a sum of the numerical values derived from pushing the plurality of first buttons and the numerical values derived from pushing the second button.

2. The diet calculator as defined in claim 1 wherein the second button has formed thereon indicia designating a "plus" sign.

3. The diet calculator as defined in claim 1 wherein the plurality of first buttons comprise at least the following groups of ingestible items;
   (a) Eggs, cheese and cereal
   (b) Bread
   (c) Juices
   (d) Dairy.

4. The diet calculator as defined in claim 1 wherein the following groups of ingestible items are contained on the plurality of first buttons;
   (a) Fresh Fruits
   (b) Drinks.

5. The diet calculator as defined in claim 1 wherein the following groups of ingestible items are contained on the plurality of first buttons;
   (a) Vegetables—Group A
   (b) Vegetables—Group B.

6. The diet calculator as defined in claim 1 wherein the following groups of ingestible items are contained on the plurality of first buttons;
   (a) Canned Fruits
   (b) Meats.

7. The diet calculator as defined in claim 1 wherein the numerical values of the first buttons represent calories of the item pushed.

8. The diet calculator as defined in claim 1 wherein the numerical values of the first buttons represent carbohydrates of the item pushed.

9. The diet calculator as defined in claim 1 wherein the numerical values of the first buttons represent proteins of the item pushed.

10. The diet calculator as defined in claim 1 wherein the plurality of first buttons comprises groups of ingestible items and caloric value range as follows;

| Item | Caloric Value Range |
|---|---|
| (a) Eggs, cheese and cereal | 75–125 |
| (b) Bread | 80–130 |
| (c) Juices | 49–100 |
| (d) Dairy | 75–105 |
| (e) Fresh Fruits | 25–127 |
| (f) Drinks | 22–65 |
| (g) Vegetables - Group A | 20–49 |
| (h) Vegetables - Group B | 22–106 |
| (i) Canned Fruits | 23–72 |
| (j) Meats | 70–250 |

11. The diet calculator as defined in claim 1 wherein the modified calculator keyboard has formed thereon the plurality of first buttons arranged in at least four rows and the caloric numerical value of each button is as follows:

| Button No. | Row No. 1 | Row No. 2 | Row No. 3 | Row No. 4 |
|---|---|---|---|---|
| 1 | 75 | 25 | 20 | 23 |
| 2 | 125 | 50 | 49 | 50 |
| 3 | 80 | 76 | 22 | 72 |
| 4 | 130 | 102 | 70 | 70 |
| 5 | 100 | 127 | 106 | 175 |
| 6 | 49 | 65 | 49 | 195 |
| 7 | 75 | 22 | — | 250 |
| 8 | 105 | — | — | — |

12. The diet calculator as defined in claim 1 wherein the modified calculator keyboard has formed thereon the plurality of first buttons arranged in at least four rows and the carbohydrate numerical value of each button is as follows:

| Button No. | Row No. 1 | Row No. 2 | Row No. 3 | Row No. 4 |
|---|---|---|---|---|
| 1 | 3 | 8 | 3 | 22 |
| 2 | 21 | 22 | 5 | 11 |
| 3 | 12 | 11 | 6 | 12 |
| 4 | 21 | 24 | 10 | 1 |
| 5 | 9 | 3 | 18 | 0 |
| 6 | 23 | 0 | 10 | 0 |
| 7 | 13 | 0 | — | 0 |
| 8 | 12 | — | — | — |

13. The diet calculator as defined in claim 1 wherein the modified calculator keyboard has formed thereon the plurality of first buttons, arranged in at least four rows and the protein numerical value of each button is as follows:

| Button No. | Row No. 1 | Row No. 2 | Row No. 3 | Row No. 4 |
|---|---|---|---|---|
| 1 | 15 | 1 | 3 | 1 |
| 2 | 2 | 1 | 3 | 1 |
| 3 | 2 | 1 | 2 | 1 |
| 4 | 3 | 1 | 2 | 8 |
| 5 | 2 | 1 | 4 | 18 |
| 6 | 2 | 4 | 1 | 32 |
| 7 | 7 | 0 | — | 30 |
| 8 | 9 | — | — | — |

14. A diet calculator, comprising:
 (a) a case;
 (b) a viewing screen, positioned within the case, wherein the viewing screen is a CRT and is capable of showing at least one item of the group of items comprising calories, carbohydrates and proteins, the viewing screen also showing a food code value adjacent to the item on the screen;
 (c) a platform weighing scale mechanism positioned partially on the exterior of the case for receiving quantities of ingestible items on the platform and positioned partially within the case;
 (d) a plurality of first buttons, positioned on the case and having positioned thereon indicia designating ingestible items;
 (e) a plurality of second buttons, positioned on the case and having positioned thereon indicia designating food code values;
 (f) a plurality of third buttons, positioned on the case and having positioned thereon indicia designating at least one item of the group of items comprising calories, carbohydrates or proteins;
 (g) a plurality of fourth buttons, positioned on the case and having positioned thereon indicia designating miscellaneous calculator functions; and
 (h) calculator means, positioned within the case, for electricaly connecting the screen, the scale mechanism, the plurality of first, second, third and fourth buttons together as a functioning calculator.

15. The diet calculator as defined in claim 14 wherein the viewing screen is a CRT and is capable of showing calories, carbohydrates and proteins.

16. The diet calculator as defined in claim 14 wherein the viewing screen is a CRT and is capable of showing calories, carbohydrates, proteins and the weight of the item placed on the scale.

17. The diet calculator as defined in claim 14 wherein the plurality of second buttons have positioned thereon indicia designating a food code which corresponds to the food code shown on the CRT.

18. A diet calculator, comprising:
 (a) a case;
 (b) a CRT viewing screen, positioned within the case, for viewing at least one item of a predetermined group of items selected by the user of the diet calculator;
 (c) a platform weighing scale mechanism positioned partially on the exterior of the case for receiving quantities of ingestible items on the platform and positioned partially within the case;
 (d) a plurality of first buttons, positioned on the case and having positioned thereon indicia designating ingestible items;
 (e) a plurality of second buttons, positioned on the case and having positioned thereon indicia designating food code values;
 (f) a plurality of third buttons, positioned on the case and having positioned thereon indicia designating at least one item of a predetermined group of items;
 (g) a plurality of fourth buttons, positioned on the case and having positioned thereon indicia designating miscellaneous calculator functions; and
 (h) calculator means, positioned within the case, for electrically connecting the screen, the scale mechanism, the plurality of first, second, third and fourth buttons together as a functioning calculator and a viewing device for viewing at least one item of a predetermined group of items.

19. The diet calculator as defined in claim 18 wherein the plurality of first buttons have positioned thereon the indicia "drinks", "breads", "desserts", "fats", "meats", "milk products", "snacks", "soups" and "vegetable fruits".

20. The diet calculator as defined in claim 18 wherein the plurality of fourth buttons comprise at least an "on/off button", a "clear" button and a "CE" button.

21. The diet calculator as defined in claim 20 wherein the plurality of fourth buttons also comprises a "diets" button.

22. A diet computer/calculator, comprising:
 (a) a case;
 (b) a weighing device comprising a weighing platform positioned on the exterior of the case and a weighing mechanism positioned within the case;
 (c) a CRT positioned within the case and having its viewing screen positioned for viewing from the exterior of the case;
 (d) a computer/calculator circuit positioned within the case and programmed and electrically connected to project on the CRT viewing screen, on command, at least one group of items of the grouping comprising ingestible items and a food code value of at least one item of the group of items comprising calories, carbohydrates or proteins;
 (e) means, electrically associated with the weighing device and the CRT, for sending a signal designating a weight of an item positioned on the weighing device to the CRT for viewing on the CRT;
 (f) a plurality of first buttons, positioned on the case and having positioned thereon indicia designating ingestible items, the first buttons being electrically connected to the computer/calculator circuit and being designed to signal the computer to project a given group of ingestible items and their food code on the CRT viewing screen;
 (g) a plurality of second buttons, positioned on the case and having positioned thereon indicia designating food code values, the second buttons being electrically connected to the computer/calculator circuit and having a designated numerical value input into the computer/calculator circuit when pushed;
 (h) a plurality of third buttons, positioned on the case and having positioned thereon indicia designating at least one item of the group of items comprising calories, carbohydrates, or proteins, the third buttons being electrically connected to the computer/calculator circuit and having designated "equal" value input into the computer/calculator circuit when pushed;
 (i) means, electrically associated with the weighing device and the computer/calculator circuit, for reading the weight of the ingestible item positioned on the platform and sending a signal to the computer/calculator to multiply the readout weight by the food code numerical values pushed on the first plurality of buttons; and (j) a plurality of fourth buttons, positioned on the case and having positioned thereon indicia designating miscellaneous calculator functions.

23. The diet computer/calculator as defined in claim 22 wherein the plurality of fourth buttons comprise at least an "on/off" button.

24. The diet computer/calculator as defined in claim 22 wherein the plurality of fourth buttons comprise at least an "on/off" button and a "clear" button.

25. The diet computer/calculator as defined in claim 22 wherein the plurality of fourth buttons comprise at least an "on/off" button, a "clear" button and a "CE" button.

* * * * *